United States Patent [19]

Gordon

[11] Patent Number: 4,781,178

[45] Date of Patent: Nov. 1, 1988

[54] ORTHOPEDIC GLOVE

[76] Inventor: Kevin M. Gordon, 10421 Summer Holly Cir., Los Angeles, Calif. 90077

[21] Appl. No.: 11,642

[22] Filed: Feb. 6, 1987

[51] Int. Cl.[4] .............................................. A61F 5/00
[52] U.S. Cl. .................................... 128/77; 128/87 A
[58] Field of Search ...................... 128/87 A, 77, 87 R, 128/26

[56] References Cited

U.S. PATENT DOCUMENTS

| | | | |
|---|---|---|---|
| 1,220,476 | 3/1917 | Ujdur | 128/87 A |
| 1,708,757 | 4/1929 | Freileweh | 128/89 R |
| 1,817,212 | 8/1931 | Siebrandt | 128/85 |
| 2,438,144 | 3/1948 | Bunyar | 128/77 |
| 4,173,218 | 11/1979 | Cronin | 128/87 A |
| 4,366,812 | 1/1983 | Nuzzo | 128/87 A |
| 4,384,571 | 5/1983 | Nuzzo et al. | 128/87 A |

FOREIGN PATENT DOCUMENTS 270341 2/1914 Fed. Rep. of Germany ... 128/87 A

Primary Examiner—Edgar S. Burr
Assistant Examiner—Huong Q. Pham
Attorney, Agent, or Firm—Nilsson, Robbins, Dalgarn, Berliner, Carson & Wurst

[57] ABSTRACT

An orthopedic glove to which one or more splints are affixed at selective locations to immobilize a joint of a particular finger and/or the wrist of the hand, while not significantly interfering with the movement of the associated metacarpal joint. This selective affixing of one or more splints to the orthopedic glove allows for the immobilization of only those joints which are afflicted by arthritis. The glove may further include independently adjustable straps which can be secured about various portions of the glove.

10 Claims, 2 Drawing Sheets

ORTHOPEDIC GLOVE

BACKGROUND OF THE INVENTION

The present invention relates to orthopedic devices, more specifically to an orthopedic glove for use with arthritically stricken hands.

Arthritis is a crippling disease which affects the joints. Literally, arthritis means "inflammation of the joint" and it can occur in any joint of the body. Of principle interest are those forms of arthritis which afflict the joints of the hand, of which the most prominent forms are osteoarthritis, rheumatoid arthritis and juvenile arthritis. It is estimated that these types of arthritis afflict millions of people in the United States alone.

While the cause of arthritis is unknown, its effect is to continually weaken and destroy the bones, cartilage and other associated tissue of the affected joint. As the various joint tissues degrade, the joint becomes inflamed making movement difficult and painful, which causes the associated muscle tissue to tighten, thus further restricting the joint mobility. The overall effect of the inflammation and degradation of the joint tissues, along with the tightening of the associated muscle tissues, is to cause the movement of that joint to become increasingly more difficult.

Since the effects of arthritis are progressive, if the disease is not checked early by proper treatment the inflammation and the stiffening of the joint becomes increasingly worse. The damage to the various tissues of the joint can become so pronounced that the joint becomes disfigured and in the most severe cases begins to assume a grotesque appearance.

While there is no known cure for arthritis, by instituting and faithfully following a treatment program during the early stages of the disease, the associated damage to the joint bones and the related tissue may be minimized. Such treatment programs include medication, exercise, rest, surgery, heat and rehabilitation. The purposes of the various treatments are to relieve both the pain and to prevent any further damage to the joint tissue by reducing the associated inflammation. The institution of a treatment program early in the development of the disease minimizes the potential of the joints becoming deformed, thus allowing the joints to move and function properly.

A particularly useful treatment for arthritis, particularly when the arthritis afflicts the hands, is to immobilize the afflicted joints, for example, the fingers and the wrist. This immobilization relaxes the muscles, preventing them from tightening up and causing further damage to the joints. Immobilization also reduces the inflammation, which reduces damage to that joint.

Immobilization of the afflicted joints can be concurrently carried out with other treatment programs, such as the application of heat to the joint, which further reduces inflammation. Medication may also be prescribed to reduce inflammation. Thus, while each particular treatment program alone may provide a desired effect, by combining various treatment programs, e.g., the immobilization of the joint, the application of heat to the joint and the use of medication, a pronounced reduction in the extreme results of arthritis is obtained, that is, joint deformity.

The afflicted joint may be immobilized by simply bracing the joint against movement. This can be accomplished by securing a splint to the limb or to that portion of the body at which the afflicted joint lies; for example, a splint can be secured about one or more of the fingers to immobilize the afflicted joints of those particular fingers. Various devices have been developed which can be fitted on the hand to immobilize the fingers and, if desired, the wrist. Examples of such devices are disclosed in U.S. Pat. Nos. 1,220,476 issued to Ujdur; 1,708,757 issued to Freileweh; 1,817,212 issued to Siebrandt; 2,438,144 issued to Bunyar, Jr.; and 4,173,218 issued to Cronin.

Generally, the devices disclosed by these patents include a rigid member which is fastened to the hand for immobilizing both the wrist and one or more of the fingers. The primary application for most of the disclosed devices is in restraining the movement of the hand and wrist in order to prevent even the slightest flexing of the fingers or wrist when one or more bones have been broken. While with arthritis it is desirable to restrict movement of the various joints, it is also known that complete immobilization may result in muscular atrophy, which in turn results in muscular contractions that disfigure the knuckles of the fingers even further.

The only device which allows for some movement of the finger joints is that device disclosed by Cronin; however, the Cronin device, which is a glove-like envelope that is filled with a fluid, is awkward to use and would be difficult and expensive to construct. One advantage of the Cronin device is that by forming the glove-like envelope with vents and/or heating elements, the fluid can be heated or cooled to further reduce joint inflammation. However, this modification to the Cronin device would even further make such device awkward to use and difficult to construct.

Thus, while presently available devices may be utilized to restrict the movement of the hand and wrist and thus reduce inflammation, there exists the need to provide a device which can be easily fitted on the hand and not present the disadvantages of the discussed devices.

SUMMARY OF THE INVENTION

The present invention overcomes the above discussed disadvantages by providing an orthopedic glove which includes a covering formed to fit over substantially the entire hand, including the wrist, to which one or more splints may be selectively and detachably affixed. The positions to which the splints may be affixed allow for the selective immobilization of only the arthritically afflicted joints, while not substantially immobilizing the metacarpal joints.

The orthopedic glove may further be formed for adjustable tightening of only desired sections of the glove about selected portions of the hand, e.g., the fingers, the thumb or the wrist, to further restrict movement of arthritically afflicted joints. This would typically include forming the glove with one or more straps that are adjustably positionable about the glove fingers and the main glove body, that is, the palm and backside of the hand and the wrist. Each one of these straps may be selectively tightened to further immobilize a desired joint or joints of the hand.

By forming the glove from a thermally insulating material the treatment of the arthritic inflammation may further be enhanced. The thermally insulating material not only provides warmth to the joints, but reduces the possibility that the joints will become subjected to rapid cooling.

DESCRIPTION OF THE DRAWINGS

The present invention will be better understood, and its numerous objectives and advantages will become apparent to those skilled in the art by reference to the accompanying figures, where like referenced numerals refer to like elements in he several figures, and wherein.

DESCRIPTION OF THE INVENTION

The invention is directed to an orthopedic glove to which one or more splints are affixed at selective locations to immobilize a joint of a particular finger (reference herein to "finger" shall include by such reference the thumb) and/or the wrist of the hand while not significantly interfering with the movement of the associated metacarpal joints. This selective affixing of one or more splints to the orthopedic glove allows for the immobilization of only those joints which are afflicted by arthritis. Furthermore, the degree of immobilization may be adjusted by the appropriate positioning of one or two splints on either side of the finger or the wrist and by adjusting the tension of straps which are secured about selected portions of the glove.

Figure 1:
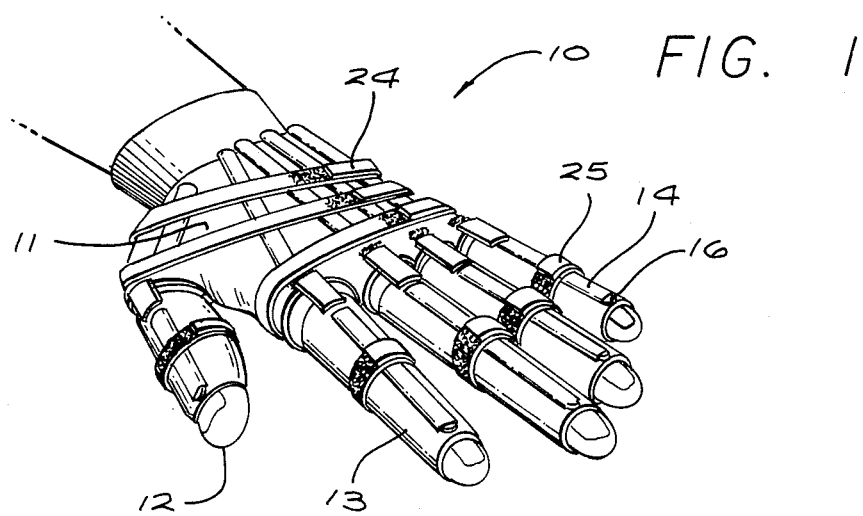
FIG. 1 is a perspective top view of an orthopedic glove in accordance with one embodiment of the invention fitted on a hand of an individual.

Referring to FIG. 1, an orthopedic glove in accordance with the invention is seen generally at 10, as placed on an individual's hand. The glove 10 includes a main body 11 which covers the wrist, back side and palm of the hand. The glove 10 also includes five tubular sleeves 13 which fit on the various fingers 12 of the hand. As will be described in more detail below, various sized splints, one of which is seen at 16, may be affixed to either or both sides of each finger sleeve 13, while not extending over the associated metacarpal joint, in order to immobilize that particular finger.

The term "metacarpal joint" shall mean that joint of the fingers formed between the distal end of the metacarpal and the proximal end of the phalanges, and for the thumb the joint between the proximal end of the first metacarpal and the trapezium.

The extent of immobilization will depend on whether one or two splints are affixed to either one or both sides of the finger sleeve 13 and the tightness of associated straps 25 described below. One or more splints, not shown, may also be affixed to either or both sides of the glove main body 11. The splints affixed to the glove body 11 should be of a sufficient length to lie over the wrist when affixed to the glove body 11. Thus by the appropriate placement of the splints on either or both sides of the glove body 11, the degree to which the wrist and hand is immobilized can be controlled.

The degree to which the hand 12 is immobilized may be further controlled by forming the glove 10 to include straps which can be adjustably tightened about the individual finger sleeves 13 and the glove body 11. For example, the illustrated glove 10 includes three body straps, one of which is seen generally at 24, which are secured at one end to the body 11 and can be adjustably tightened about various portions of the body 11. The glove 10 also includes-single straps, one of which is seen at 25, secured to and adjustably tightenable about each of the individual finger sleeves 13. Preferably, each individual strap 25 is secured to the respective sleeve to allow for tightening about the respective main carpal joint of the finger 12, one of which is seen generally at 13.

By tightening a strap 25 about the associated finger sleeve 13 to which one or more splints have been affixed, the degree of immobilization is enhanced. The glove 10 of the invention thus allows for the overall control of the immobilization of the joints of the various fingers and the wrist of the hand by the selective affixing of splints to the glove body 11 and/or finger sleeves 13 and by the selective tightening of the variously positioned straps, while at the same time allowing flexing of the fingers since the metacarpal joints are not immobilized.

It should be noted that the sides of the fingers and hand being referred to herein are those sides lying along the backside of the hand and the hand palm. The affixing of the splints along these sides will restrict the movement of the various joints between the phalanges (fingers) and the trapezium (thumb), as well as the joints between the carpals (wrist).

Figure 2:
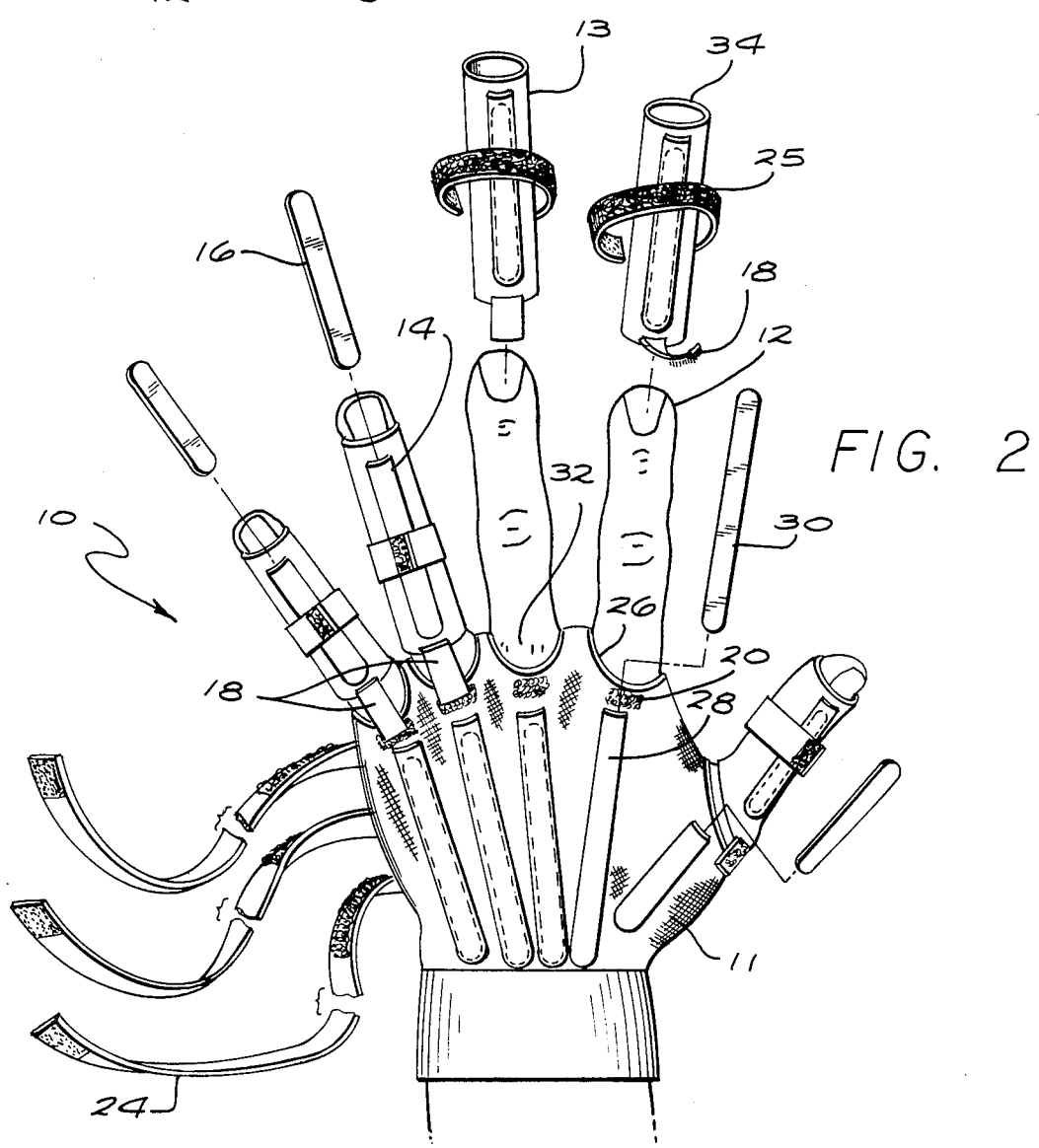
FIG. 2 is a top, partially exploded view of the orthopedic glove shown in FIG. 1.
Figure 3:
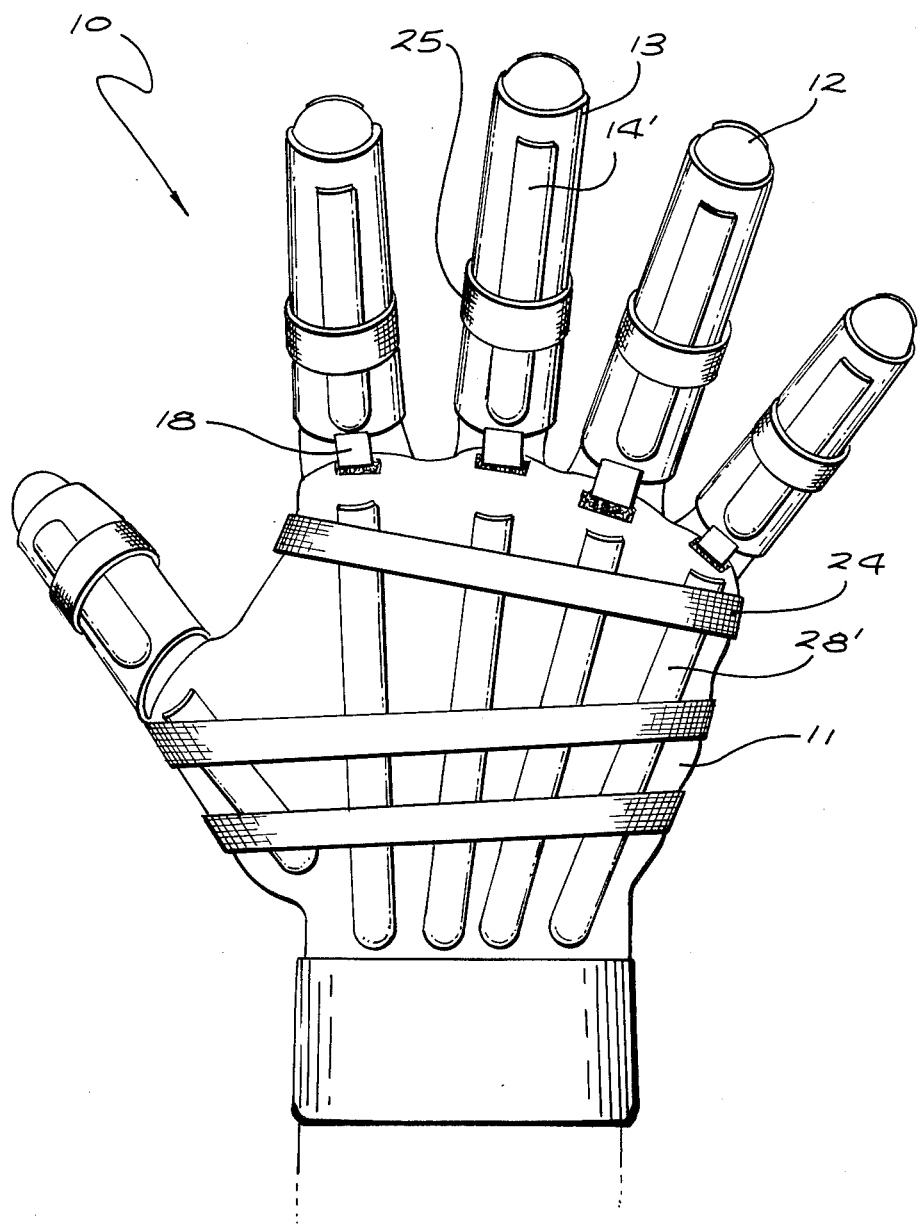
FIG. 3 is a bottom view of the orthopedic glove shown in FIG. 2.

Referring to FIGS. 2 and 3, the glove 10 of the invention will be described in greater detail. As stated, the glove 10 is formed with five finger sleeves 13 that extend out from a glove body 11. As seen in FIG. 2, the finger sleeves 13 are each elongated tubular bodies which are detachable from the glove body 11. In this regard, each sleeve 13 has secured at one end a strip of Velcro material, indicated generally at 18, with a compatible Velcro strip, one of which is seen at 20, secured to the glove body 11 at a location contiguous to one of various holes, one of which being indicated at 26, through which the fingers 12 will extend out of the body 11. Thus the individual sleeves 13 are slipped onto the desired fingers 12 and secured to the glove body 11 by adhering the Velcro strips 18 and 20 together. While the illustrated embodiment utilizes Velcro to attach the sleeves 13 to the glove body 11, any suitable attachment mechanism may be used.

As stated, each of the individual sleeves 13 is suitably formed with pockets, one of which is seen at 14, into which an appropriately sized splint 16 is inserted. Each of these pockets 14 runs substantially along the entire length of each sleeve 13. As illustrated, the individual finger sleeves 13 will each be formed with two opposing pockets 14 and 14', with pocket 14 seen in FIG. 2 on the back side of the finger 12 and the pocket 14' seen in FIG. 3 on the palm side of the finger 12. This allows the mobility of each finger 12 to be selectively reduced by inserting one or both of the splints 16 into the respective pockets 14 or 14' of each individual sleeve 13.

The glove body 11 is also formed with various elongated pockets running substantially along the entire length of both the back side and palm side of the hand. These pockets, with the back side pockets seen in FIG. 2 at 28 and the palm side pockets seen in FIG. 3 at 28', are formed on the glove 10 so that when the glove 10 is positioned upon the individual's hand, they will be substantially aligned over the hand metacarpals and overlay the carpals of the wrist. In this regard, the glove body 11 is formed with five pockets 28 and 28' on both sides.

Further, each one of the pockets 28 formed in the back side portion of the glove body 11 will be substantially aligned with a pocket 28' on the palm side of the glove body 11. This allows the selective immobilization of the hand, including the wrist, by inserting into one or both of the opposing pockets 28 and 28' appropriately sized splints, one of which is seen generally at 30 in FIG. 2.

However, the glove body 11 need only be formed with a sufficient number of pockets to allow for the immobilization of the wrist, since this is the primary joint the splints affixed to the glove body 11 are meant to restrain.

In the illustrated embodiment, the various pockets 14 and 14' formed on the finger sleeves 13 will be substantially aligned with one of the glove body pockets 28 or 28', respectively, when the sleeves 13 are secured to the body 11. However, neither the finger section pockets 14 or 14' nor the glove body pockets 28 or 28' will lie over the metacarpal joint, one of which is indicated generally at 32 in FIG. 2, of the individual fingers 12 as a result of the sleeves 13 being detachable from the body 11.

This assures that the movement of that metacarpal joint 32 associated with that particular finger 12 will be not immobilized and will not be interfered with when the splints 16, 16' and 30, 30' are inserted in their respective pockets. This allows the metacarpal joints to freely move even when all of the various splints 16, 16' and 30, 30' are inserted in their respective pockets. By allowing even slight movement of the metacarpal joints, muscular atrophy is substantially avoided and use of the hand is increased and encouraged.

The glove 10 is further formed with various straps, indicated at 24 and 25, which are independently and adjustably bindable about various portions of the glove body 11 and the individual sleeves 13. The straps 24 and 25 are formed to be adjustably tightened about that portion of the glove 10 to which they are secured. By tightening the respective straps 24 or 25 about its respective glove body 11 or sleeve 13, the mobility of the hand 12 and associated fingers is further restricted. This immobility is increased if the associated splints 16 or 30 have been placed in their respective pockets.

Thus by combining the immobilizing action of the splints 16 and 30 with the binding effect of the straps 24 and 25, the degree to which the hand palm, wrist and individual fingers 12 are immobilized can be selected by the individual wearing the glove 10. That is, the individual, by either loosening or tightening the individual straps 24 or 25 and by the selective insertion of the individual splints 30 and 16 into their respective pockets, can determine the degree to which his palm, wrist and fingers will be immobilized. This allows the individual to not interfere with the movement of those fingers which are either not afflicted with arthritis or not severely enough afflicted.

While any suitable adjustable strap arrangement can be utilized, the individual straps 24 and 25 are formed from Velcro strips, that is, the individual straps 24 and 25 are formed by securing a length of the hooked portion of the Velcro back-to-back with a length of the looped portion. This allows for the adjustable tightening of the individual straps 24 and 25 about, for example, a single finger sleeve 13.

As seen in FIGS. 2 and 3, each of the finger sleeves 13 are formed at their ends opposite the end secured to the glove body 11 with holes, one of which is seen at 34, through which the respective finger tip will extend. This allows visual observation of the condition of each finger to assure that a proper amount of blood is reaching the fingers despite the restriction caused by the affixing of the splints to and the binding of straps about the glove 10.

The individual splints 16 or 30 are constructed from a substantially rigid material and are generally planar. This material may include, for example, wood or metal. It is further within the scope of the invention to provide splints of different lengths and constructed from materials of differing degrees of stiffness for use with the glove 10. That is, the glove 10 can be provided with splints 30 and 16 of varying stiffness. This would allow an individual to select a splint of a desired stiffness or length for affixing to the glove 10 in order to increase or decrease the immobility of a particular joint.

The orthopedic glove of the invention may be constructed from any suitable material, such as cotton or one of the numerous synthetic or blended fabrics. It is also envisioned that the orthopedic glove 10 be constructed from a material which can breathe, thus allowing comfort to the individual wearer or from a thermal insulating material, which would provide warmth to the underlying joints. This would allow the therapeutic value of the orthopedic glove 10 to not only be derived from the immobilization of particular joints but also from the warmth directed to those joints as a result of the glove 10 being constructed from a thermal insulating material.

In accordance with another embodiment, the glove 10 can be formed with the finger sleeves 13 being integral with the body 11. That is, the finger sleeves 13 would not be detachable from the body 11. This would not interfere with the overall usefulness of the invention, since the individual would be able to select which finger to immobilize by the insertion of the splints 16 into the respective pocket 14 or 14'. However, the various pockets of the glove finger sections, as well as the various pockets of the glove body, should not extend over the various metacarpal joints in a manner which would significantly interfere with the movements of these joints.

While the preferred embodiments have been described and illustrated, various modifications and substitutions can be made thereto without departing from the scope of the invention. Accordingly, it is understood that the present invention has been described by way of illustration and not limitation.

What is claimed is:

1. An orthopedic glove comprising:
   a hand covering having a main section adapted to cover a hand, including a hand palm side and a back side, said main section of said hand covering having a plurality of elongated pockets formed on both said back side and said palm side;
   a plurality of separate detachable finger sleeve sections, each of said separate sleeve sections being formed with two sleeve pockets, said sleeve pockets being positioned on opposite sides of said finger sleeve section;
   mounting means for selectively and removably mounting selected ones of said finger sleeve sections to said main section at one or more of five different locations, each of said five locations being selected to be adjacent to a respective one of said hand fingers; and
   elongated splints adapted to be selectively and removably insertable into each of said main section pockets and said finger sleeve pockets.

2. The glove of claim 1 further including first strap means connected to said glove main section which are selectively adjusted for securing and tightening said covering main section about selective portions of said hand while in use.

3. The glove of claim 1 further including second strap means connected to each of said finger sleeve sections which are selectively adjusted for securing and tightening each of said finger sleeve sections about said finger while in use.

4. The glove of claim 2 wherein said two opposite finger sleeve pockets are positioned on those opposing sides of said fingers which are substantially equivalent to said palm and back side, and wherein none of said finger sleeve pockets extends over a metacarpal joint associated with that respective finger.

5. The glove of claim 4 wherein five pockets are formed on said covering main section palm and back sides for receiving said splints.

6. The glove of claim 5 wherein each of said pockets formed on said covering main section palm side and each of said pockets formed on said covering main section back side are individually positioned over a hand metacarpal and aligned with one of said pockets on the opposing side of said covering main section.

7. The glove of claim 6 wherein said glove covering is comprised of a thermally insulating material.

8. The glove of claim 7 wherein a first end of said finger sleeves are formed to include holes out through which a portion of said respective hand finger extends.

9. The glove of claim 14 wherein said mounting means comprises two pieces of a first material secured at opposite sides to each of said sleeve section and two pieces of a second material secured at opposite sides to each of said five locations of said main section, with said first material including hook portions and said second material including mateable loop portions.

10. An orthopedic glove comprising:
a hand covering having a main section adapted to cover a hand, including a hand palm side and a back side, said main section of said hand covering having a plurality of elongated pockets formed on both said back side and said palm side;
a plurality of separate detachable finger sleeve sections, each of said separate sleeve sections being formed with two sleeve pockets, said pockets being positioned on opposite sides of said finger sleeve;
non-rigid mounting means for selectively and removably mounting selected ones of said finger sleeve sections to said main section at one or more of five different locations, each of said five locations being selected to be adjacent to a respective one of said hand fingers, said mounting means mounting said finger sleeves to said main section in a spatially separated relationship, whereby said finger sleeve pockets are not positioned over that matacarpal joint of said finger; and
elongated splints adapted to be selectively and removably insertable into each of said main section pockets and said finger sleeve pockets.

* * * * *

UNITED STATES PATENT AND TRADEMARK OFFICE
CERTIFICATE OF CORRECTION

PATENT NO. : 4,781,178
DATED : November 1, 1988
INVENTOR(S) : Kevin M. Gordon

It is certified that error appears in the above-identified patent and that said Letters Patent is hereby corrected as shown below:

Column 3, line 7 delete "he" and insert --the--

Column 3, line 66 delete "-"

Column 7, line 28 delete "14" and insert --8--

Signed and Sealed this

Twenty-first Day of March, 1989

Attest:

DONALD J. QUIGG

*Attesting Officer*   *Commissioner of Patents and Trademarks*